United States Patent
Tseng et al.

(10) Patent No.: US 9,546,349 B2
(45) Date of Patent: Jan. 17, 2017

(54) SUPPORTS FOR CELL CULTURE AND CELL SHEET DETACHMENT AND METHODS FOR CELL SHEET DETACHMENT

(75) Inventors: How Tseng, Taipei (TW); Jeng-Kuen Tsai, Taipei (TW); Keng-Liang Ou, Taipei (TW); Po-Nien Chen, Taipei (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 317 days.

(21) Appl. No.: 13/118,990

(22) Filed: May 31, 2011

(65) Prior Publication Data
US 2012/0309089 A1    Dec. 6, 2012

(51) Int. Cl.
*C12M 1/26* (2006.01)
*C12N 5/00* (2006.01)
*C12M 1/12* (2006.01)

(52) U.S. Cl.
CPC ............ *C12M 25/00* (2013.01); *C12M 25/06* (2013.01); *C12M 33/00* (2013.01); *C12N 5/0068* (2013.01); *C12N 2533/30* (2013.01); *C12N 2533/40* (2013.01)

(58) Field of Classification Search
CPC . C12M 25/00; C12N 2533/40; C12N 2533/30

USPC ........................................................ 435/378
See application file for complete search history.

(56) References Cited

U.S. PATENT DOCUMENTS

2004/0028657 A1\* 2/2004 Okano et al. ................ 424/93.7
2009/0117656 A1\* 5/2009 Akashi et al. ................ 435/397

OTHER PUBLICATIONS

Hironobu Takahashi et al., Controlled Chain Length and Graft Density of Thermoresponsive Polymer Brushes for Optimizing Cell Sheet Harvest, Biomacromolecules, 2010, pp. 1991-1999, vol. 11, No. 8.

\* cited by examiner

*Primary Examiner* — Sharmila G. Landau
*Assistant Examiner* — Sheridan MacAuley
(74) *Attorney, Agent, or Firm* — WPAT, P.C., Intellectual Property Attorneys; Anthony King

(57) ABSTRACT

The invention creates a support for cell culture and cell sheet detachment which has a substrate, whose surface is coated with a conjugate having a disulfide bond-containing amino acid as a spacer and a biopolymer enhancing cell attachment, migration or differentation. Unexpectedly, after being seeded on the support, the cells grow to form one or more layers of cell sheets and the cell sheets can be easily detached from the support by adding a reductant to cleave the disulfide bond. Accordingly, the invention provides a simple and non-toxic method for detachment of cell sheets.

14 Claims, 1 Drawing Sheet

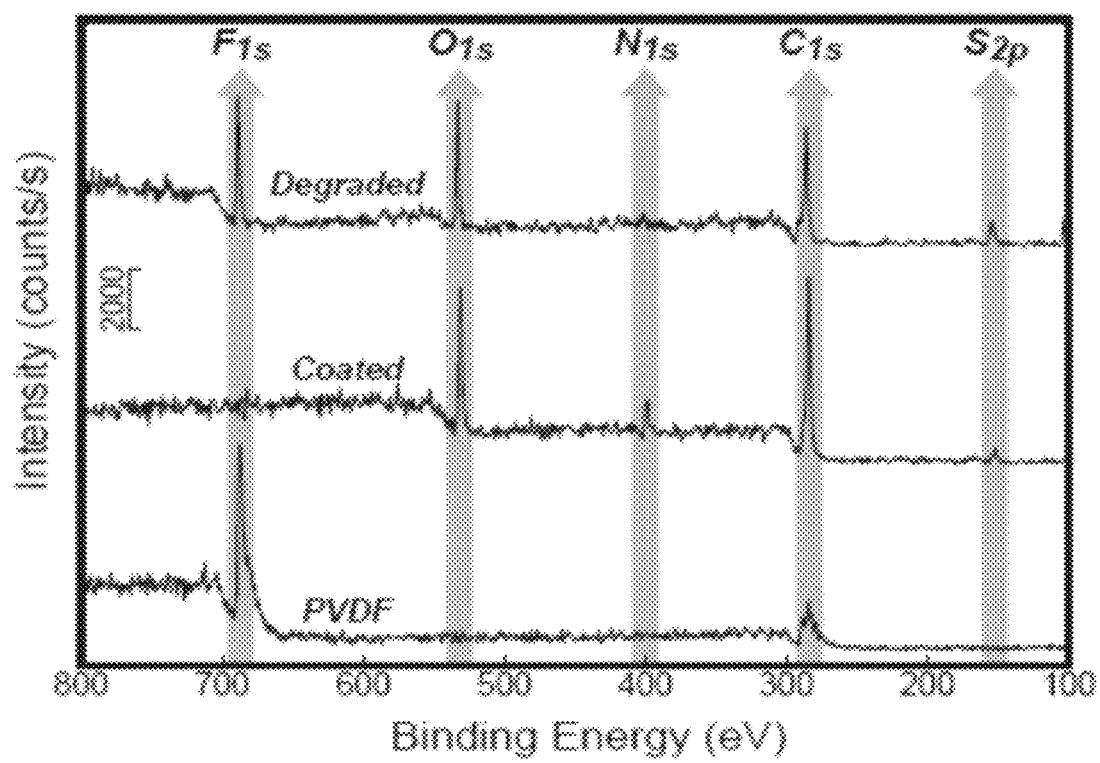

SUPPORTS FOR CELL CULTURE AND CELL SHEET DETACHMENT AND METHODS FOR CELL SHEET DETACHMENT

FIELD OF THE INVENTION

The invention provides a support for cell culture and cell sheet detachment, a method for preparation of the support and a method for the detachment of cell sheets from a culture container. In particular, the support comprises a biocompatible, non-biodegradable polymer substrate, which on its surface covalently links a conjugate.

BACKGROUND OF THE INVENTION

Tissue engineering has become a key therapeutic tool in the treatment of damaged or diseased organs and tissues, such as blood vessels and urinary bladders. Tissue engineering seeks to provide regenerated tissue architectures in vitro, but has not yet successfully created thick, highly vascularized, multi-functional tissues replicating native structure. Cell sheet engineering has been proposed to overcome the problems of tissue engineering. Cell sheet engineering can avoid tissue reconstruction limitations using biodegradable scaffolds or single cell suspension injection. Such a cell sheet constructed in vitro could be useful in various clinical situations to regenerate tissues (especially epithelial tissues) such as artificial skin and artificial cornea.

Cell sheets can be prepared using cells from various biological tissues and organs. These can be used alone as tissue for transplantation or in combination with sheets composed of other cells, and can be used either singly or in stacked arrangements of multiple cell sheets. Cells normally attach strongly to hydrophobic surfaces but weakly to hydrophilic surfaces. When cells are cultured in a normal container such as culture dish, they proliferate and make a monolayer sheet. The cells are structurally connected to each other by intercellular junction proteins and adhere to the surface of the culture dish with adhesive proteins. In the art, in order to detach the cell sheet from the dish, proteolytic enzymes are normally used to disrupt the adhesive proteins. However, in such a releasing procedure using a proteolytic enzyme, not only may the cells be damaged, but also the extracellular matrix produced during the culture may be decomposed. Furthermore, since most proteolytic enzymes are materials derived from animals, the application of such proteolytic enzymes to a cell sheet for regenerative medicine is problematic in terms of safety. Therefore, it is desirable to recover the monolayer cells in a cell sheet structure at the end of the culture stage without using a biochemical or chemical reagent.

Subsequently, cell sheets are developed with thermo responsive culture dishes. Thermo responsive polymers are grafted to dishes covalently, which allows different cell types to attach and proliferate at 37° C. Cells detach spontaneously when temperature decreases to below 32° C., without the need to use enzymes, and this is due to the natural specification of the intelligent polymers also due to the detachment of the cell metabolic changes made by the polymer resulting from decreasing temperature. U.S. Pat. No. 6,956,077 discloses a polymer compound which undergoes stretching and cohesion with a change in the polarity of the polymer per se due to a temperature change, a process for producing this polymer compound, a heat-responsive polymer material containing this compound, a separation method with the use of a material containing this heat-responsive polymer material, and a method for separating chemicals, biological polymers (proteins, peptides, etc.) and biological samples (cells, etc.) by using this material. Hironobu Takahashi et al. demonstrated surface-initiated RAFT technique to materialize new type thermoresponsive N-isopropylarylamide (PIPAAm) brush surfaces for cell sheet harvest (*Biomacromolecules*, "Controlled Chain Length And Graft Density Of Thermoresponsive Polymer Brushes For Optimizing Cell Sheet Harvest" Vol. 11, No. 8, 2010, pp. 1991-1999). US 2006240552 A1 provides an anterior ocular segment related cell sheet or three-dimensional structure and a process for producing the anterior ocular segment related cell sheet or three-dimensional structure by using a temperature responsive polymer having an upper or lower critical dissolution temperature of 0-80° C. US 20080131476 A1 provides a cultured cell sheet with good tissue adherence and flexibility which is obtained by culturing cells on a support for cell culture in which a surface of a substrate is coated with a temperature-responsive polymer having an upper or lower critical dissolution temperature of 0-80° C. along with a surfactant protein or a crosslinking inhibitor.

However, the above-mentioned prior references use thermoresponsive polymers grafted on the surface of a culture dish and control temperature to release the cultured cells. The monomers (such as PIPAAm) of the polymers may remain in the culture dish so as to bring toxicity and the temperature control procedure is not simple. Therefore, there is a need to develop a substrate with low toxicity and improved cell attachment and detachment and a process of simply detaching cell sheets from the cultured container.

SUMMARY OF THE INVENTION

The invention provides a support for cell culture and cell sheet detachment, comprising a biocompatible substrate, whose surface is coated with a conjugate having the formula —P-L-S—S—R—K-Q through a peptide bond of —C(=O) NH—, wherein L and R may be the same or different and independently represent a thiol-containing amino acid residue; —S—S represents a disulfide bond that is formed by oxidation of thiol groups of L and R; P and K may be the same or different and independently represent 0-3 amino acid residue(s); and Q is a biopolymer.

The invention also provides a culture container which has the support of the invention.

The invention further provides a method for production of the support of the invention for cell culture and cell sheet detachment, comprising the steps of:
(a) generating a carboxyl group (—COOH) on the surface of a substrate; and
(b) covalently linking a conjugate having the formula —P-L-S—S—R—K-Q to the substrate by directly condensating the carboxyl group (—COOH) of the substrate and the amino group of P of the conjugate, or in situ, one by one synthesizing P, L, R, K and Q of the conjugate on the substrate, presynthesizing one or more fragments of the conjugate having the formula —P-L-S—S—R—K-Q and then in situ linking the fragments on the substrate, wherein L and R may be the same or different and independently represent a thiol-containing amino acid residue; —S—S represents a disulfide bond that is formed by oxidation of thiol groups of L and R; P and K may be the same or different and independently represent 0-3 amino acid residue(s); and Q is a biopolymer whereby a support comprising a substrate which on its surface covalently links a conjugate having the formula —P-L-S—S—R—K-Q through a peptide bond of —C(=O)NH— is obtained.

The invention also further provides a method for detachment of cell sheet from a culture container having the support of the invention, comprising the steps of: (a) culturing cells in a culture container having the support of the invention to form cell sheet, and (b) adding a reductant to cleave the disulfide bond in the conjugate of the support of the invention so that the cell sheet is detached from the surface of the container.

The invention also further provides a cell sheet, which is obtained from the cell sheet detachment method of the invention.

BRIEF DESCRIPTION OF THE DRAWING

FIG. 1 shows the spectrum of PVDF wherein fluoride (F) at 690 eV is equivalent to carbon (C) at 400 eV in intensity, and no peak of nitrogen (N) appears at 400 eV. In contrast, nitrogen (N) peak appears in the spectrum of the coated PVDF membrane.

DETAILED DESCRIPTION OF THE INVENTION

The invention creates a support for cell culture and cell sheet detachment which has a substrate, whose surface is coated with a conjugate having a disulfide bond-containing amino acid as a spacer and a biopolymer enhancing cell attachment, migration or differentiation. Unexpectedly, after being seeded on the support, the cells grow to form one or more layers of cell sheets and the cell sheets can be easily detached from the support by adding a reductant to cleave the disulfide bond. Accordingly, the invention provides a simple and non-toxic method for detachment of cell sheets.

As used herein, the term "residue" refers to the portion of a molecule remaining after reaction with one or more molecules. For example, an amino acid residue in a conjugate of the invention typically corresponds to the portion of the amino acid up to but excluding the covalent linkage resulting from reaction of a reactive group on the amino acid with a reactive group on an entity in the conjugate of the invention.

As used herein, the term "conjugate" is intended to refer to the entity formed as a result of covalent attachment of a molecule, e.g., an amino acid molecule(s) to a biocompatible material or a biopolymer.

As used herein, the term "cell" or like term refers to a small usually microscopic mass of protoplasm bounded externally by a semipermeable membrane, optionally including one or more nuclei and various other organelles, capable alone or interacting with other like masses of performing all the fundamental functions of life, and forming the smallest structural unit of living matter capable of functioning independently including synthetic cell constructs, cell model systems, and like artificial cellular systems.

As used herein, the terms "attach," "attachment," "adhere," "adhered," "adherent," or like terms generally refer to immobilizing or fixing, for example, a group or a compound, and to a surface, such as by physical absorption, chemical bonding, and like processes, or combinations thereof.

Support for Cell Culture and Cell Sheet Detachment and Culture Container Having the Support In one aspect, the invention provides a support for cell culture and cell sheet detachment, comprising a biocompatible substrate, which on its surface, is coated with a conjugate having the formula —P-L-S—S—R—K-Q through a peptide bond of —C(=O)NH—, wherein L and R may be the same or different and independently represent a thiol-containing amino acid residue; —S—S represents a disulfide bond that is formed by oxidation of thiol groups of L and R; P and K may be the same or different and independently represent 0-3 amino acid residue(s); and Q is a biopolymer.

According to the invention, any suitable biocompatible material can be used as the substrate of the invention. Examples of such substrates include, but are not limited to, glass, quarts, quartz glass, and the following polymer segments or polymers: poly(ethylene terephthalate) (PET), polyethylene, polyvinyl difluoride (PVDF), polydimethylsiloxane (PDMS), polytetrafluoroethylene (PTFE), polystyrene (TCPS), polymethylmethacrylate (PMMA), polycarbonate, polyolefin, ethylene vinyl acetate, polypropylene, polysulfone, polytetrafluoroethylene, silicones, poly(meth)acrylic acid, polyamides, polyvinyl chloride, polyvinylphenol, and copolymers and mixtures thereof. Preferably, the substrate is transparent. More preferably, the substrate is glass, quarts, quartz glass, poly(ethylene terephthalate) (PET), polyethylene, polyvinyl difluoride (PVDF), polydimethylsiloxane (PDMS), polytetrafluoroethylene (PTFE) and polystyrene (TCPS). Preferably, the substrate is transparent. More preferably, the substrate is TCPS, PET, PVDF, glass, quarts or quartz glass. More preferably, the substrate is transparent TCPS, PET, PVDF, glass, quarts or quartz glass. More preferably, the substrate is transparent PVDF.

According to the invention, the substrate may be a membrane with smooth or porous surface or a soft-lithography patterned membrane.

According to the invention, a conjugate having the formula —P-L-S—S—R—K-Q covalently links on the surface of the substrate through a peptide bond of —C(=O)NH—, wherein L and R may be the same or different and independently represent a thiol-containing amino acid residue; —S—S represents a disulfide bond that is formed by oxidation of thiol groups of L and R; P and K may be the same or different and independently represent 0-3 amino acid residue(s); and Q is a biodegradable biopolymer.

According to the invention, L and R may be the same or different and independently represent a thiol-containing amino acid residue. Preferably, the thiol-containing amino acid residue is a cysteine, cystamine or homocysteine residue.

According to the invention, —S—S represents a disulfide bond that is formed by oxidation of thiol groups of L and R. Disulfide bonds are usually formed from the oxidation of —SH functional group.

According to the invention, P and K may be the same or different and independently represent 0-3 amino acid residue(s). Preferably, P and K is glycine, alanine, valine, leucine, isoleucine, methionine, proline, phenylalanine, tryptophan, serine, threonine, glutamine, tyrosine, cysteine, lysine, arginine, asparagine, histidine, glutamic acid or aspartic acid. More preferably, P and K are glycine, alanine, valine, proline, threonine, cyseine, leucine or isoleucine. More preferably, P and K are absent.

According to the invention, Q is a biopolymer, preferably, a natural biopolymer. The biopolymer of the invention can improve cell attachment, proliferation, migration or differentiation. There are seven general classes of the biopolymers: polynucleotides, polyamides, polysaccharides, polyisoprenes, polyphosphate and polyhydroxyalkanoates. Preferably, the biodegradable biopolymer is polylysine, gamma-polyglutamic acid (γ—PGA), collagen, chitosan, hyaluronic acid (HA), gelatin, polylactides (PLA) or polyglycolides.

The support of the invention is used for cell culture and detachment of cell sheets. According to the invention, the cell sheet can be monolayer or multilayer. A number of cell types may be cultured on the support of the invention using standard cell culturing techniques. Typically the cells used in the invention comprise adherent cell types. Such cells when cultured under appropriate conditions divide and expand to cover and adhere to a cell growth substrate. The cell types may be allogeneic or autologous with respect to a subject to which that a tissue construct derived from the cells is ultimately implanted or used. Examples of the cells include corneal cells, chondrocytes, osteoblasts, fibroblasts, epidermal cells, epithelial cells, adipocytes, hepatocytes, pancreatic cells, muscle cells, and precursor cells thereof, mesenchymal stem cells, and embryonic stem cells (ES cells).

In another aspect, the invention provides a culture container which has the support for cell culture and cell sheet detachment of the invention.

According to the invention, a culture container includes any number of materials and compositions, many of which are currently commercially available, including for example, a culture vessel, a culture flask, a culture well insert, a culture plate of a rectangular or circular shape having a growth area of about 1 cm² to greater than 500 cm², a multiwell culture plate having 2 wells to more than 90 wells, and a specimen slide as used in microscopic analysis. Other cell growth surfaces and devices are readily apparent to those of skill in the art.

A sheet grown from various cell types are grown for periods of days to weeks in a culture container. Typically the cell sheets are grown for about 1-24 weeks, depending on the application, donor age, viability of the particular cell population, and the like.

In most cell culture applications, adherent cell cultures can only be maintained for a few days to a few weeks before the cells release from a substrate. The addition of agents that promote cell growth, viability and/or adhesion can be used during the culture process. For example, agents such as ascorbic acid, retanoic acid, and copper can be added to increase the production of extracellular matrix proteins thereby generating a more robust tissue sheet of cells. Moreover, by treating the cell culture surface/substrate with extracellular matrix proteins or other factors (e.g., a protein such as gelatin or fibrin), adhesion can be prolonged.

Method for Production of the Support of the Invention for Cell Culture and Cell Sheet Detachment In another aspect, the invention further provides a method for production of the support of the invention for cell culture and cell sheet detachment, comprising the steps of:
  (a) generating a carboxyl group (—COOH) on the surface of a substrate; and
  (b) covalently linking a conjugate having the formula —P-L-S—S—R—K-Q to the substrate by directlycondensatingthe carboxyl group (—COOH) of the substrate and the amino group of P of the conjugate, or in situ, one by one synthesizing P, L, R, K and Q of the conjugate on the substrate, presynthesizing one or more fragments of the conjugate having the formula —P-L-S—S—R—K-Q and then in situ linking the fragments on the substrate, wherein L and R may be the same or different and independently represent a thiol-containing amino acid residue; —S—S represents a disulfide bond that is formed by oxidation of thiol groups of L and R; P and K may be the same or different and independently represent 0-3 amino acid residue(s); and Q is a biopolymer;
whereby a support comprising a substrate, which on its surface covalently links a conjugate having the formula —P-L-S—S—R—K-Q through a peptide bond of —C(=O)NH— is obtained.

In one embodiment of the invention, a carboxyl group (—COOH) in the substrate is generated on the surface thereof by plasma treatment. Preferably, the plasma treatment is $CO_2$ or $N_2$ plasma treatment.

According to the invention, a conjugate having the formula —P-L-S—S—R—K-Q links to the substrate by directly condensating the carboxyl group (—COOH) of the substrate and the amino group of P of the conjugate —P-L-S—S—R—K-Q. Alternatively, P, L, R, K and Q of the conjugate can be in situ synthesized one by one to form the structure —P-L-S—S—R—K-Q on the substrate. Alternatively, the fragments of the formula —P-L-S—S—R—K-Q can be pre-synthesized and then in situ linking these fragments on the substrate.

In one embodiment, after step (a), the resulting substrate —COOH can further react with a carbodiimide for conjugation (Bauminger and Wilchek, Meth. Enzymol. 70:151-159 (1980)). Carbodiimides comprise a group of compounds that have the general formula RN=C=NR', where R and R' can be aliphatic or aromatic, and are used for synthesis of polypeptide bonds. The preparative procedure is simple, relatively fast, and carried out under mild conditions. Carbodiimide compounds attack carboxylic groups to change them into reactive sites for free amino groups. Preferably, the carbodiimide is N-hydroxysuccinimide, 1-ethyl-3-(3-dimethylaminopropyl) carbodiimide (EDC), DCC(N,N'-dicyclohexylcarbodiimide) or DIC(N,N'-diisopropylcarbodiimide) or a mixture thereof. More preferably, the carbodiimide is EDC.

An amino acid having disulfide bond is then reacted with the resulting substrate-carbodiimide conjugate to form a substrate-amino acid residue-S—S-amino acid residue. Subsequently, a biopolymer is conjugated to the amino acid residue to form substrate-amino acid residue-S—S-amino acid residue-biopolymer through carbodiimide conjugation reaction. The amino acid residue and biopolymer are as defined above.

Method for Detachment of Cell Sheet from Surface of Culture Container and Cell Sheet Obtained Therefrom In a further aspect, the invention provides a method for detachment of cell sheet from a culture container having the support of the invention, comprising the steps of: (a) culturing cells in a culture container having the support of the invention to form cell sheet, and (b) adding a reductant to cleave the disulfide bond in the conjugate of the support of the invention so that the cell sheet is detached from the surface of the container. Accordingly, the invention also provides a cell sheet which is obtained from the above method of the invention. In the embodiment of the invention, the cell sheet can be monolayer or multiplayer.

According to the invention, thiols can be used as the reductants cleaving the disulfide bond in the conjugate of the material. Preferably, the reductant is glutathione, 2-hydroxy-1-ethanethiol, cysteine, homocysteine, mercaptoethanol (ME), dithiothreitol (DTT) or tris(2-carboxyethyl)phosphine (TCEP).

By using the support and detachment method of the invention, cell sheets with advantageous tissue adherence and flexibility can be obtained and these cell sheets can be easily and efficiently detached from a culture container. The resulting cell sheets remain intact state and can be applied in various human autografting products.

EXAMPLE

Example 1

Preparation of the Material for Cell Sheet Culture of the Invention

The Controls of Film-Forming Ability and Transparence

In addition to film-forming ability, high transparency is a preferred property of suitable substrate materials. However, PVDF commercial products are non-transparent white, similar to a Teflon membrane. The present invention provides transparent PVDF membranes.

After trying a variety of solvents, PVDF was obtained by dissolving in N-methylpyrrolidone (NMP) and casting the solution with various thicknesses on glass. The PVDF membrane directly obtained by casting and then drying was a non-transparent white film. Surprisingly, it was found that further heating the non-transparent PVDF membrane after finishing the casting would cause it to turn transparent. Such transparent appearance of the PVDF membrane meets the practical requirements of the present invention.

The Coating of Natural Biopolymer

The prepared transparent PVDF membrane was respectively treated with $CO_2$ and/or $N_2$ plasma, and then was coated by a natural biopolymer which was obtained by the crossing of Cystine, and gamma-polyglutamic acid (γ—PGA) with the mixture of N-hydroxysuccinimide and 1-Ethyl-3-(3-dimethylaminopropyl)carbodiimide. The contact angle of the coated PVDF membrane was measured to determine the coating character.

Measurements of the membrane treated with $CO_2$ plasma show that the surface of the coated PVDF membrane was combined with γ—PGA in the form of covalent bonds on the grounds that the contact angle decreased from 72.83° (pure PVDF) to 42.20°, so hydrophilicity obviously increased. Similarly, the results measured on the membrane treated with $N_2$ plasma show that the contact angle decreased from 70.98° (pure PVDF) to 30.26°, so hydrophilicity obviously increased in this case as well.

To understand whether the surface of the PVDF membrane resulting from the preparation process is satisfactory, Electron Spectroscopy for Chemical Analysis (ESCA) was also employed to measure the surface. FIG. 1 shows that in the spectrum of PVDF, fluoride (F) at 690 eV is equivalent to carbon (C) at 400 eV in intensity, and no peak of nitrogen (N) appears at 400 eV. In contrast, nitrogen (N) peak appears in the spectrum of the coated PVDF membrane. The following table shows peaks of the relevant elements. For PVDF membrane, the proportion of carbon to nitrogen is about 1:1, and for coated or degraded PVDF membrane, the proportion of nitrogen (N) of γ—PGA and sulfur (S) of Cysteine is also expected.

| Sample | At. % | | | | | |
|---|---|---|---|---|---|---|
| | C 1s | O 1s | N 1s | F 1s | S 2p | Total |
| PVDF membrane | 77.96 | 10.96 | x | 11.08 | x | 100 |
| Coated PVDF membrane | 70.77 | 19.15 | 8.08 | 0.6 | 1.4 | 100 |
| Degraded PVDF membrane | 64.17 | 17.6 | 3.26 | 14.23 | 0.74 | 100 |

Example 2

Cell Sheet Detachment Assay

Fibroblast cell line NIH3T3 was assayed for biological compatibility and cell detachment. It was found that the grafted PVDF membrane has high biological compatibility and is able to increase cell proliferation in the biological compatibility assay. For the cell detachment assay, after seeding for 24 hours, NIH3T3 was treated with reduced Cysteine. After treatment for 3 hours, the fusiform cells converted into round cells and were detached from the membrane. The detached cells were collected and placed on TCPS dishes. It was found that the cells would attach to the surface and proliferate again.

What is claimed is:

1. A support for cell culture and cell sheet detachment, consisting of a biocompatible substrate with carboxyl groups on the surface thereof, wherein the surface is in situ grafted with a conjugate having the formula -L-S—S—R-Q through a peptide bond of —C(=O)NH—, wherein L and R each represent a cysteine residue; —S—S represents a disulfide bond that is formed by oxidation of thiol groups of L and R; and Q is a biopolymer; wherein L links to the biocompatible substrate and wherein the biocompatible substrate is transparent TCPS, PET, PVDF, glass, quartz or quartz glass, and wherein Q of the conjugate is, gamma-polyglutamic acid (γ-PGA), collagen, or hyaluronic acid.

2. The support of claim 1, wherein the biocompatible substrate is transparent PVDF.

3. The support of claim 1, wherein the cell sheet is a monolayer or multilayer.

4. The support of claim 1, wherein the cell sheet is from corneal cells, chondrocytes, osteoblasts, fibroblasts, epidermal cells, epithelial cells, adipocytes, hepatocytes, pancreatic cells, muscle cells, and precursor cells thereof, mesenchymal stem cells or embryonic stem cells (ES cells).

5. The support of claim 1, wherein the substrate may be a membrane with smooth or porous surface or a soft-lithography patterned membrane.

6. A culture container, which has the support of claim 1.

7. The culture container of claim 6, which is a culture vessel, a culture flask, a culture well insert, a culture plate or a multiwell culture plate.

8. A method for production of a support for cell culture and cell sheet detachment, comprising the steps of:
  (a) generating a carboxyl group (—COOH) on the surface of a substrate; and
  (b) covalently linking a conjugate having the formula -L-S—S—R-Q to the substrate by directly condensating the carboxyl group (—COOH) of the substrate and the amino group of L of the conjugate, or in situ, one by one synthesizing, L, R, and Q of the conjugate on the substrate, presynthesizing one or more fragments of the conjugate having the formula -L-S—S—R-Q and then in situ linking the fragments on the substrate, wherein L and R each represent a cysteine residue; —S—S represents a disulfide bond that is formed by oxidation of thiol groups of L and R; and Q is a biopolymer;

whereby a support comprising a substrate, which on its surface covalently links a conjugate having the formula -L-S—S—R-Q through a peptide bond of —C(=O) NH— is obtained.

9. The method of claim 8, wherein a carboxyl group (—COOH) is generated on the surface of a biocompatible, non-biodegradable polymer substrate by plasma treatment.

10. The method of claim 9, wherein the plasma treatment is $CO_2$ or $N_2$ plasma treatment.

11. A method for detachment of cell sheet from a culture container having the support of the invention, comprising the steps of: (a) culturing cells in a culture container having the support of claim 1 to form cell sheet, and (b) adding a reductant to cleave the disulfide bond in the conjugate of the support of claim 1 so that the cell sheet is detached from the surface of the container.

12. The method of claim 11, wherein the cell sheet can be monolayer or multiplayer.

13. The method of claim 11, wherein the reductant is a thiol.

14. The method of claim 11, wherein the reductant is glutathione, 2-hydroxy-1-ethanethiol, cysteine, homocysteine, mercaptoethanol (ME), dithiothreitol (DTT) or tris(2-carboxyethyl)phosphine (TCEP).

\* \* \* \* \*